(12) United States Patent
Milledge et al.

(10) Patent No.: US 7,747,302 B2
(45) Date of Patent: *Jun. 29, 2010

(54) METHOD FOR INTEGRATING FACILITATED BLOOD FLOW AND BLOOD ANALYTE MONITORING

(75) Inventors: Eric Milledge, Belle Mead, NJ (US); Mahyar Z. Kermani, Pleasanton, CA (US)

(73) Assignee: Lifescan, Inc., Milpitas, CA (US)

( * ) Notice: Subject to any disclaimer, the term of this patent is extended or adjusted under 35 U.S.C. 154(b) by 96 days.

This patent is subject to a terminal disclaimer.

(21) Appl. No.: 11/836,030

(22) Filed: Aug. 8, 2007

(65) Prior Publication Data

US 2009/0043177 A1 Feb. 12, 2009

(51) Int. Cl.
*A61B 5/145* (2006.01)

(52) U.S. Cl. .................... 600/341; 600/316; 600/365

(58) Field of Classification Search .......... 600/310, 600/316, 322, 341, 347, 365
See application file for complete search history.

(56) References Cited

U.S. PATENT DOCUMENTS

| | | | |
|---|---|---|---|
| 5,411,551 A | 5/1995 | Winston et al. | |
| 6,132,371 A * | 10/2000 | Dempsey et al. | 600/300 |
| 6,162,611 A | 12/2000 | Heller et al. | |
| 6,360,888 B1 | 3/2002 | McIvor et al. | |
| 6,558,321 B1 | 5/2003 | Burd et al. | |
| 6,741,877 B1 | 5/2004 | Shults et al. | |
| 6,770,729 B2 | 8/2004 | Van Antwerp | |
| 6,926,670 B2 | 8/2005 | Rich et al. | |
| 7,074,307 B2 | 7/2006 | Simpson et al. | |
| 7,110,803 B2 | 9/2006 | Shults et al. | |
| 2003/0032892 A1 | 2/2003 | Van Erlach et al. | |
| 2004/0176672 A1 | 9/2004 | Silver et al. | |
| 2005/0148832 A1 | 7/2005 | Reghabi et al. | |
| 2005/0165317 A1 | 7/2005 | Turner et al. | |
| 2005/0245799 A1 | 11/2005 | Brauker et al. | |
| 2005/0245971 A1 | 11/2005 | Brockway et al. | |

FOREIGN PATENT DOCUMENTS

WO  WO 2005/046467 A1  5/2005

OTHER PUBLICATIONS

Daeyoung Kim, et al., "Measurements of Small-Scaling Fading and Path Loss for Long Range RF Tags", Antennas & Propagation, IEEE Transactions on, vol. 51, No. 8. pp. 1740-1749, Aug. 2003.
Ken'ichi Takahata, et al., "Antenna Stents for Pressure and Flow Monitoring", SSEL Annual Report 2004, p. 146.
Constatine A. Balanis, "Traveling Wave and Broadband Antennas", Antenna Theory Analysis and Design, Third Edition, 2005, pp. 566-576, Wiley-Interscience, by John Wiley & Sons, Hoboken, New Jersey.

* cited by examiner

*Primary Examiner*—Eric F Winakur
*Assistant Examiner*—Etsub D Berhanu (57) ABSTRACT

A method for the integrated facilitization of blood flow and monitoring of blood analyte concentration (for example, blood glucose concentration) includes implanting a stent configured to facilitate blood flow into a cardiovascular system of a user's body with the stent having attached thereto a continuous blood analyte determination module of a blood analyte monitoring system. The method also includes disposing a reader module of the blood analyte monitoring system external to the user's body and in proximity to a portion of the user's skin layer and monitoring blood analyte concentration via (i) emitting an RF carrier signal from the reader module toward the stent; (ii) receiving the RF carrier signal at a reflection antenna of the continuous blood analyte determination module; (iii) reflecting a modulated signal by the reflection antenna with the modulated signal being encoded with a blood analyte concentration determined by a sensor of the continuous blood analyte determination module; (iv) receiving the modulated signal by the reader module; and (v) decoding the analyte concentration from the modulated signal by the reader module.

9 Claims, 9 Drawing Sheets

METHOD FOR INTEGRATING FACILITATED BLOOD FLOW AND BLOOD ANALYTE MONITORING

BACKGROUND OF THE INVENTION

The present invention is related to the following co-pending U.S. application: U.S. patent application Ser. No. 11/835,992, filed on Aug. 8, 2007.

1. Field of the Invention

The present invention relates, in general, to medical devices and, in particular, to blood analyte monitoring devices and associated methods.

2. Description of Related Art

Continuous glucose monitors (CGM's) that are disposed (e.g., implanted) within a user's body can have limited operational lifetimes due to, for example, fouling of the CGM. Such fouling can be the result of tissue build-up or blood clotting. In addition, a challenge exists with respect to providing CGM's with a lifetime power source and providing for wireless communication with the CGM.

Many people with diabetes also have cardiac problems. For example, it is believed that thirty percent of people who could benefit from the facilitated blood flow provided by an implanted stent also have diabetes. Thus, a significant proportion of people who are in need of a stent also have a need for continuous glucose monitoring to help with their diabetic disease state.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like labels indicate like elements, of which:

DETAILED DESCRIPTION OF ILLUSTRATIVE EMBODIMENTS OF THE INVENTION

Figure 1:
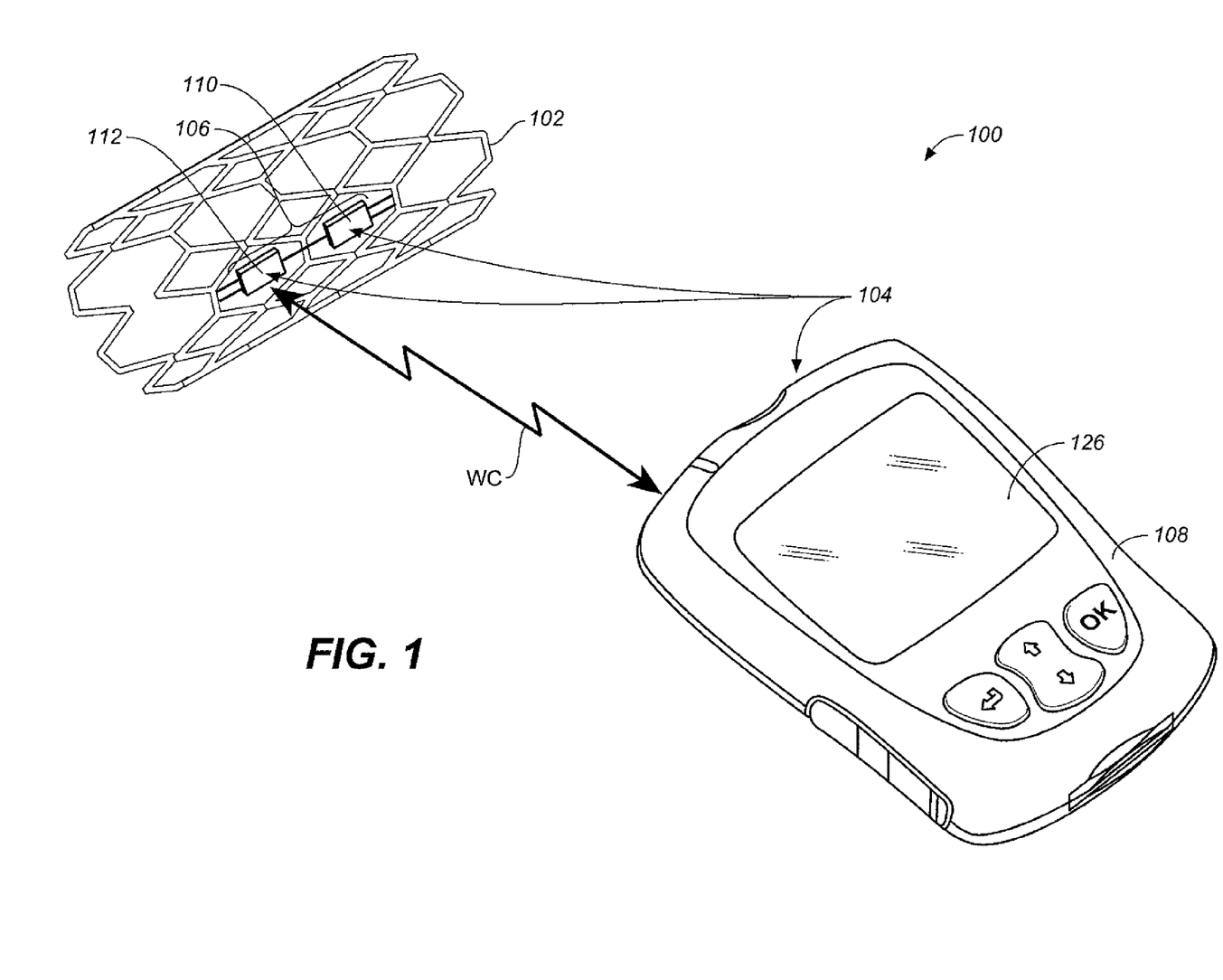
FIG. 1 is a simplified perspective view of an integrated stent and blood analyte monitoring system according to an exemplary embodiment of the present invention.
Figure 2:
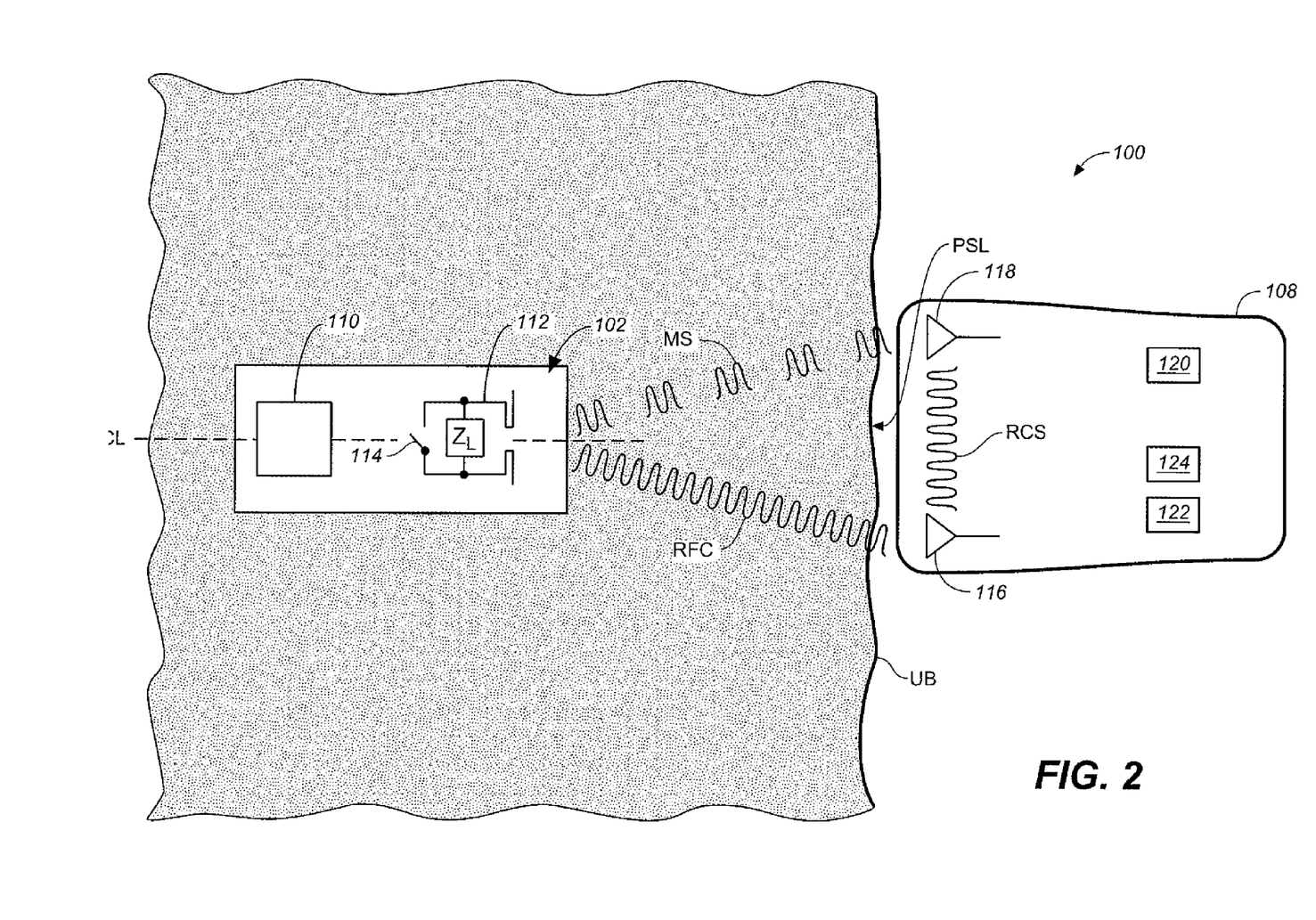
FIG. 2 is a simplified combined block diagram and schematic illustrating the system of FIG. 1 in use.

FIG. 1 is a simplified perspective view of an integrated stent and blood analyte monitoring system 100 according to an embodiment of the present invention. FIG. 2 is a simplified combined block and schematic diagram illustrating use of integrated stent and blood analyte monitoring system 100. In FIG. 1, a two-way wireless communication signal is depicted by a double-headed arrow WC. Such a two-way wireless communication signal is described in more detail below with respect to FIG. 2.

Referring to FIGS. 1 and 2, integrated stent and blood analyte monitoring system 100 is configured for integrated facilitization of blood flow and blood analyte monitoring and includes a stent 102 and a blood analyte monitor system 104. Moreover, blood analyte monitor system 104 includes a continuous blood analyte determination module 106 (attached to stent 102) and a reader module 108.

Stent 102 is configured for implantation into a cardiovascular system of a user's body (UB, see, for example, FIG. 2) and has a longitudinal centerline CL (see FIG. 2). Stent 102 is depicted in FIG. 1 as a mesh-shaped stent. However, stents of any suitable configuration can be employed in embodiments of the present invention including, for example, helical-shaped and cylindrical-shaped stents.

Moreover, stents employed in embodiments of the present invention can, if desired, include a drug eluting coating (not shown in the FIGs.) to prevent clot formation and/or build up of new tissue. An example of a commercially available stent with a drug eluting coating is the CYPHER® stent from Cordis, Inc., which is coated with Sirolimus. Such a stent could be readily modified for employment in embodiments of the present invention.

Stents employed in embodiments of the present invention can also coated with a macrolide antibiotic that suppresses an immune response of the user or a clot inhibiting reagent such as, for example, heparin. It is expected that preventing the formation of a clot and/or tissue build-up on continuous blood analyte determination module 106 will provide for the stabile operation of the continuous blood analyte determination module since clot formation or tissue build-up would deleteriously interfere with the mass diffusion of an analyte (for example, glucose) to a sensor of the continuous blood analyte determination module.

Continuous blood analyte determination module 106 has a sensor 110 configured for determining the concentration of a blood analyte and a reflection antenna 112. Moreover, reflection antenna 112 has a switch 114.

The sensor employed in embodiments of the present invention can be, for example, an electrochemical glucose sensor or an optical glucose sensor. In addition, such an electrochemical glucose sensor can be either an amperometric or a potentiometric sensor. Examples of electrochemical sensor which can be readily modified for use in embodiments of the present invention are described in U.S. Pat. Nos. 7,110,803; 6,741,877; 6,558,321; 7,074,307; 6,360,888; and 6,162,611, and U.S. Patent Application Publications No.'s 2005/0148832 and 2005/0245799, each of which are hereby fully incorporated by reference herein.

Reader module 108 is configured for disposition external to the user's body and proximal to a portion of the user's skin layer (PSL). Moreover, reader module 108 is configured to emit a radio frequency (RF) carrier signal RFC toward stent 102. Reader module 108 also includes a first antenna 116, a second antenna 118, a lock-in amplifier 120, microprocessor block 122, memory block 124, and display 126.

In the embodiment of FIGS. 1 and 2, first antenna 116 is configured to emit (i.e., transmit) RF carrier signal RFC toward stent 102. Reflection antenna 112 is configured to receive RF carrier signal RFC and reflect a modulated signal MS back to reader module 108 (see FIG. 2). In addition, modulated signal MS has been modulated by switch 114 (in the embodiment of FIGS. 1 and 2, reflection antenna 112 has an electrical impedance ZL that is modulated by switch 114 as a means of creating modulated signal MS) such that modulated signal MS is encoded with an analyte concentration (for example, a blood glucose concentration) determined by sensor 110. Reader module 108 is configured to receive the modulated signal MS using second antenna 118 and decode the analyte concentration therefrom. Reader module 108 is also configured to display the decoded analyte concentration on display 126 for viewing by the user. Once apprised of the present disclosure, one skilled in the art will recognize that reader module 108 can be, for example, a hand-held episodic glucose meter.

Modulated signal MS may be a relatively weak signal. Therefore, reader module 108 includes lock-in amplifier 120 to aid in the detection and amplification of modulated signal MS using techniques known to one skilled in the art. In the embodiment of FIGS. 1 and 2, reference RF carrier signal (RCS) is employed as a reference for tuning a lock-in amplifier 120. Reader module 108 decodes signal MS using microprocessor block 122 and stores the decoded analyte concentration in memory block 124 using decoding and storage techniques that are known to one skilled in the art.

One skilled in the art will recognize that switch 114 may be opened and closed with a predetermined pattern to modulate first RF carrier signal RFC as a means for encoding data, such as a glucose concentration, for transmission to reader module 108 as modulated signal MS. The use of a reflection antenna and a switch 114 serves to beneficially decrease the power consumption of the continuous blood analyte determination modules. The operation of switch 114 may consume a small amount of power. In an embodiment of this invention, stent 102 may have a battery (not shown) to power the continuous blood analyte determination module (for example, to and for open and close switch 114). Alternatively, RF carrier signal RFC can be converted by reflection antenna 112 to an electrical current for operating switch 114 and optionally for operating continuous blood analyte determination module 106.

Figure 3:
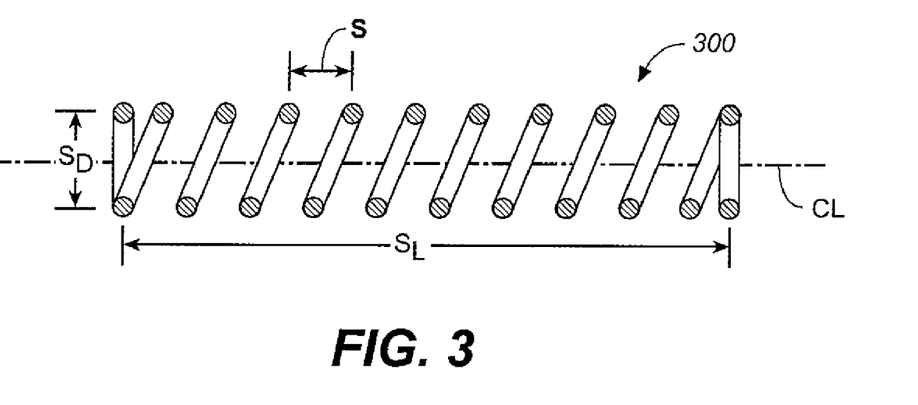
FIG. 3 is a simplified cross-section representation of a helical stent as can be employed in embodiments of the present invention.
Figure 4:
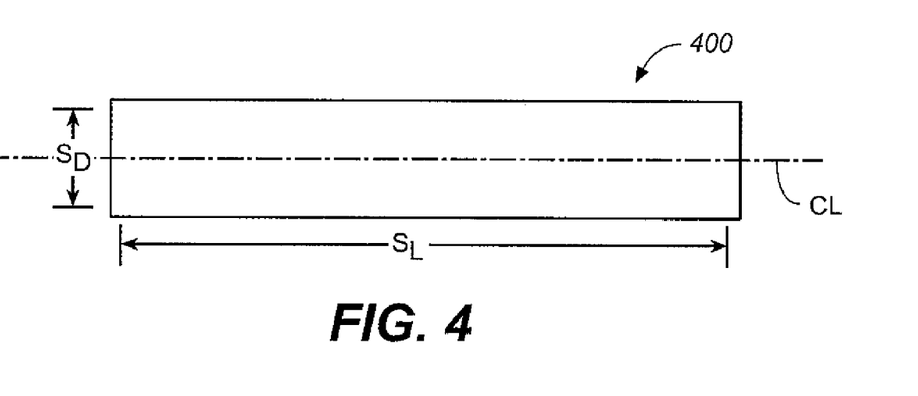
FIG. 4 is a simplified depiction of a cylindrical stent as can be employed in embodiments of the present invention.

FIG. 3 is a simplified cross-section representation of a helical stent 300 as can be employed in embodiments of the present invention. FIG. 4 is a simplified depiction of a cylindrical stent 400 as can be employed in embodiments of the present invention.

Referring to FIGS. 3 and 4, stents 300 and 400 are each configured with a stent length $S_L$ and a stent diameter $S_D$. Stents 300 and 400 each have a longitudinal center lime CL as depicted by the dashed lines of FIGS. 3 and 4. Stent 300 is formed as a helical coil with a coil spacing S.

In embodiments of the present invention, the stent itself (such as helical stent 300 of FIG. 3 or the mesh stent of FIG. 1), or a portion thereof can serve as the reflection antenna. In such a circumstance, the stent performs both the function of a reflection antenna and the function of facilitating blood flow through the user's cardiovascular system. It is an advantage of this invention to use the stent itself as a reflection antenna since such a configuration simplifies manufacturing.

Figure 5:
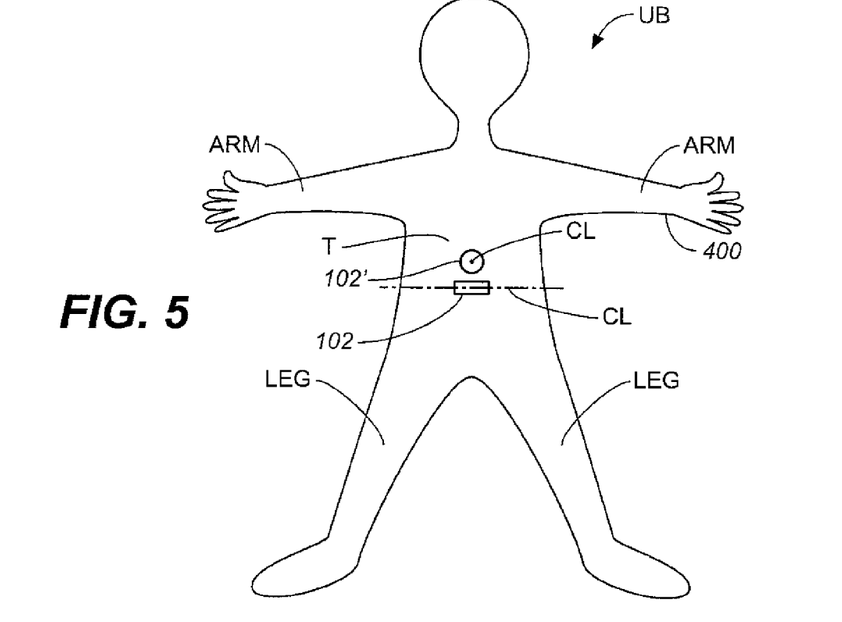
FIG. 5 is a simplified depiction of a two stents implanted in a torso of a user with the stents orientated such that a center line of each of the stents is perpendicular to a portion of the user's skin layer.

FIG. 5 is a simplified depiction of a two stents (102 and 102') implanted in a torso T of a user's body UB with stents 102 and 102' orientated such that a center line (CL) of each of the stents is perpendicular to a portion of the user's skin layer. For stent 102 in FIG. 5, the relevant portion of the user's body (i.e., the portion of the user's body to which the CL is perpendicular) is the side of the torso. For stent 102' it is the front of the torso.

Figure 6:
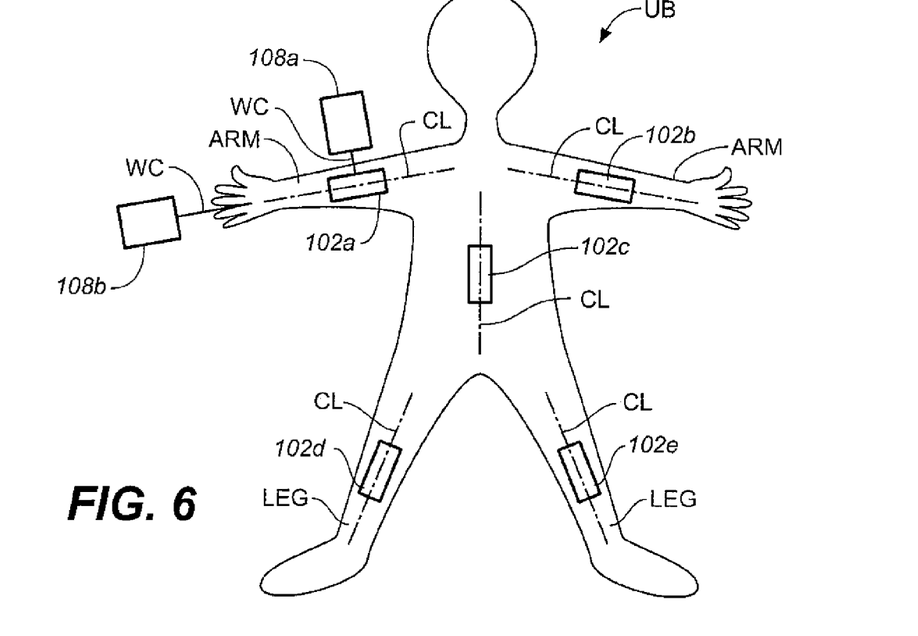
FIG. 6 is a simplified depiction of five stents implanted in a user's body with the stents oriented such that a center line of each of the stents is parallel to a portion of the user's skin layer.

FIG. 6 is a simplified depiction of five stents (102a, 102b, 102c, 102d and 102e) implanted in a user's body UB with the stents oriented such that a center line (CL) of each of the stents is parallel to a relevant portion of the user's skin layer. For example, the center line of stents 102d and 102e is parallel to the skin of the user's leg in which each of the stents is implanted. Also shown in FIG. 6 are two reader modules 108a and 108b disposed external to the user's body. During use of systems according to embodiments of the present invention, a reader module can be positioned on an arm (ARM), leg (LEG) or torso (T) of a user's body (i.e., on a portion of the user's skin layer that is in close proximity to an implanted stent and continuous blood analyte determination module). The reader module can be dispositioned such that wireless communication WC (i.e., signals RFC and MS) travels through the relevant portion of the user's skin layer (see for example, the disposition of reader 108 in FIG. 2, the disposition of reader module 108a in FIG. 6, and the descriptions below related to FIGS. 7 through 13).

Referring to FIG. 6, reader module 108b is positioned such that wireless communication WC travels approximately parallel to a portion of the user's skin layer but is not in close proximity to implanted stent 102a. An examination of FIG. 6 indicates that directing wireless communication parallel to a user's skin limits the ability for a reader module to be positioned close to a stent. Therefore, in embodiments of the present invention, it is preferred that the reader module emit an RF carrier signal that is not parallel to the portion of the user's skin layer but rather at a predetermined non-parallel angle as described further herein, for example below with respect to FIGS. 7 through 13.

Stents and continuous blood analyte monitoring modules employed in embodiments of the present invention can be implanted into the cardiovascular system of a user in two orientations, either with center line perpendicular to a portion of the user's skin layer (see FIG. 5) or parallel to a portion of the user's skin layer (see FIG. 6). The orientation of FIG. 5 is also referred to as an "axial" or "endfire" orientation. The orientation of FIG. 6 is also referred to as a "normal" or "broad side" orientation.

In general, the cardiovascular system is orientated parallel to a user's skin layer for appendages such as arms and legs. However, portions of the cardiovascular system can be orientated either parallel or perpendicular in the torso area. Stents implanted in the torso area are often implanted in a vessel near the heart. As a consequence, stents implanted in the arms and legs typically have a center line CL parallel to user's skin layer, as illustrated in FIG. 6. Stents implanted in an area around torso may have a center line CL parallel or perpendicular to user's skin layer, as illustrated in FIGS. 5 and 6.

A simulation was performed to determine a suitable configuration of first antenna 116 and second antenna 118 where both are positioned adjacent to a portion of a user's skin layer. The simulation assumed a helical coil-shaped stent having a stent length $S_L$ ranging from about 8 millimeters to about 33 millimeters, and a stent diameter $S_D$ ranging from about 2 millimeters to about 5 millimeters.

First RF carrier signal RFC was assumed to have a frequency ranging from about 402 MHz to about 405 MHz, which is the medical implant communication service (MICS) band as defined by the FCC. Since reader module 108 is typically configured to be dispositioned (i.e., placed) immediately against skin layer of user's body UB, RF carrier signal RFC and modulated signal MS will predominantly travel through the skin tissue, which was assumed to have a dielectric constant of 58. The simulation indicated that a coil spacing S ranging from about 0.5 millimeters per turn to about 3 millimeters per turn is suitable for a reflection antenna to transmit data using a modulated backscattered method of data transmission.

The simulation was performed using a MATLAB computer program, entitled Helix, designed to analyze a helical antenna. The computer program was obtained as a multimedia CD with a book entitled Antenna Theory, Analysis and Design by Constantine A. Balanis (pages 566-576, $3^{rd}$ edition, 2005, Wiley-Interscience, A John Wiley & Sons, Inc.). The software modeled the angular attenuation of a helical antenna for orientations where the center line CL of the stent was perpendicular and parallel to a user's skin layer as shown by Equation 1.

$$[\theta,\rho] = f(S/\lambda, C/\lambda, N) \quad \text{Eq. 1}$$

The term $\lambda$ represents the wavelength of RF carrier signal RFC, C represents the circumference of the helix which is directly proportional to stent diameter $S_D$, N represents the number of turns on the helix, $\theta$ represents the angle with respect to the center line CL, and $\rho$ represents the amount of attenuation in decibels (dB's).

Figure 7:
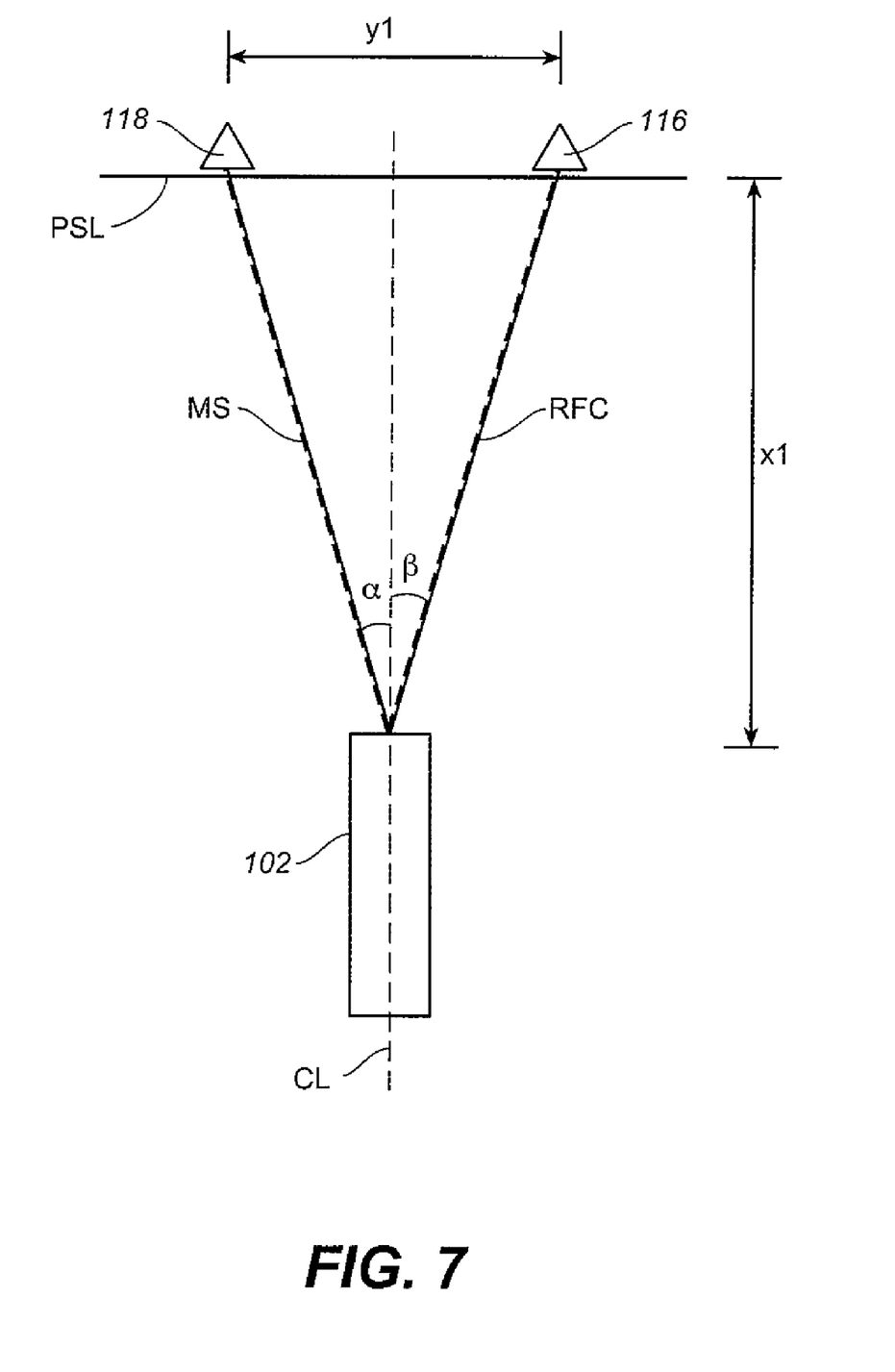
FIG. 7 is a simplified schematic diagram depicting an implanted stent being interrogated by a first and second antenna disposed immediately adjacent to a portion of a user's skin layer wherein a center line of the stent is perpendicular to the portion of the user's skin layer.
Figure 8:
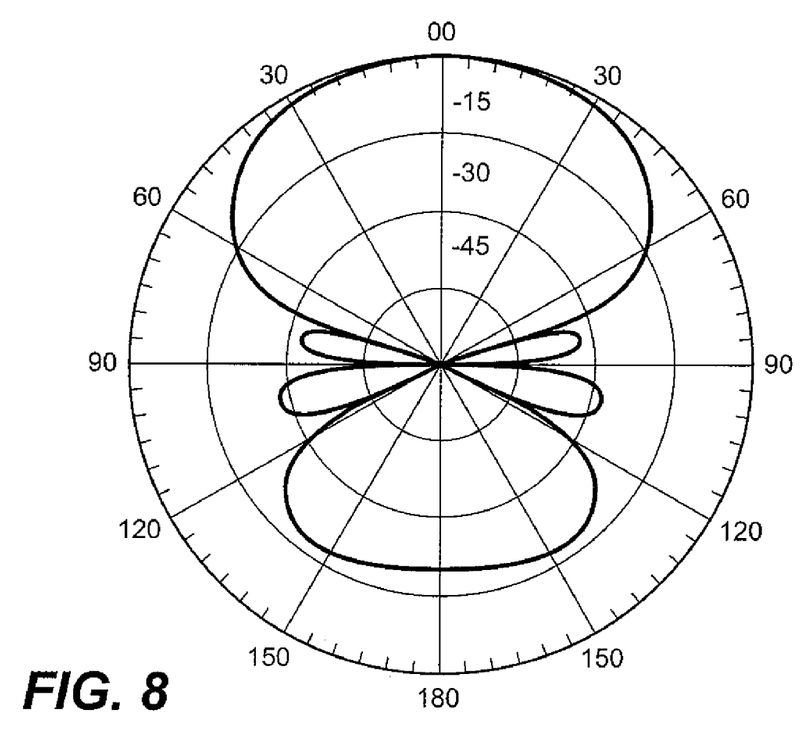
FIG. 8 is a simplified two-dimensional graph illustrating attenuation of an RF carrier signal after being reflected at a spectrum of angles for a configuration wherein a center line of a stent is orientated perpendicular to a portion of a user's skin layer.
Figure 9:
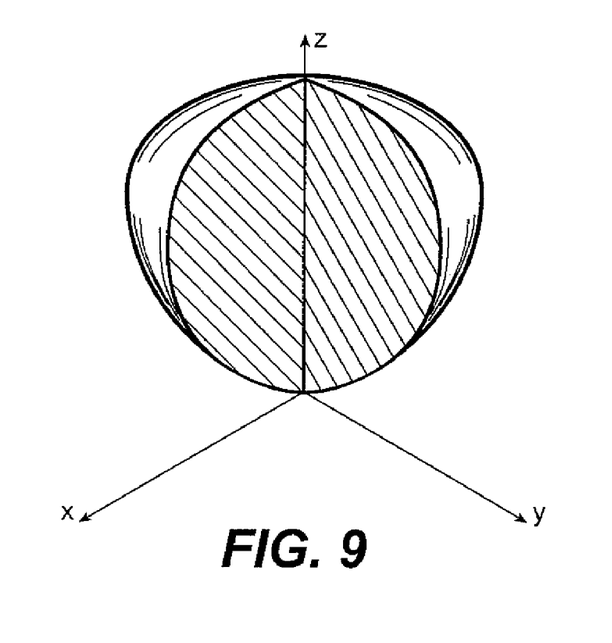
FIG. 9 is a simplified three-dimensional graph (corresponding to FIG. 8) illustrating a balloon shaped lobe that has the lowest attenuation of the RF carrier signal after being reflected at a spectrum of angles.

FIG. 7 is a simplified schematic diagram depicting an implanted stent 102 being interrogated by a first and second antenna (116 and 118) disposed immediately adjacent to a portion of a user's skin layer PSL wherein a center line CL of stent 102 is perpendicular to the portion of the user's skin layer PSL. FIG. 8 is a simplified two-dimensional graph illustrating attenuation of an RF carrier signal after being reflected at a spectrum of angles for a configuration wherein a center line of a stent is orientated perpendicular to a portion of a user's skin layer PSL (as in FIG. 7). FIG. 9 is a simplified three-dimensional graph (corresponding to FIG. 8) illustrating a balloon shaped lobe that has the lowest attenuation of the RF carrier signal after being reflected at a spectrum of angles.

FIGS. 8 and 9 indicate that a lobe having the lowest attenuation of RF carrier signal RFC forms a balloon shape in three dimensions. The center line CL of stent 102 is coincident with a line formed along the 0 degree and 180 degree portion of FIG. 8. Moreover, modulated signal MS forms a modulated signal angle α with the center line CL. FIG. 8 shows that there is a low amount of attenuation (e.g., less than about −3 dB) when modulated signal angle α is less than about 30 degrees.

Referring to FIG. 7, first antenna 116 directs first RF carrier signal RFC towards stent 102 at an RF carrier signal angle β with respect to center line CL. Second antenna 118 is dispositioned to receive modulated signal MS, which is reflected from stent 102 at a modulated signal angle α with respect to the center line CL. Both first antenna 116 and second antenna 118 are at a distance X1 from stent 102 when positioned against portion of user's skin layer PSL. Distance Y1 is the distance between first antenna 116 and second antenna 118. Based on the attenuation of modulated signal MS as shown in FIG. 8, it is preferred that both first antenna 116 and second antenna 118 be positioned such that RF carrier signal angle β and modulated signal angle α are less than about 30 degrees.

There is a trigonometric relationship between modulated signal angle α, RF carrier signal angle β, distance X1, and distance Y1 as shown in Equation 2.

$$\alpha = \beta = \tan\frac{\frac{Y1}{2}}{X1} \quad \text{Eq. 2}$$

For the situation in which center line CL of the stent is perpendicular to the user's skin layer, the angular range (α and β summed together) was derived using an electronic simulation (as depicted in FIG. 8). The estimated angular range and the distance Y1 between first antenna 116 and second antenna 118 can be predetermined using Equation 1 to effectively interrogate a stent at a typical distance X1 underneath the user's skin layer.

Distance X1 can be, for example, in range from about 5 millimeters to about 40 millimeters, and preferably between about 20 millimeters to about 30 millimeters. Assuming that first antenna 116 and second antenna 118 are positioned against a portion of user's skin layer PSL, first antenna 116 and second antenna 118 will be a distance X1 away from the stent 102.

In the orientation of FIG. 7, if the angular range is too large (i.e., greater than +/−30 degrees), then modulated signal MS may be too attenuated for a wireless reading to be performed. Because first antenna 116 and second antenna 118 occupy a finite space, distance Y1 generally cannot be less than about 5 millimeters. Additionally, distance Y1 must be sufficiently large so as to prevent second antenna 118 from becoming saturated by a reference RF carrier signal RCS.

Distance Y1, which separates first antenna 116 and second antenna 118, can be in the range of from about 5 millimeters to about 50 millimeters, and preferably may be about 25 millimeters. Distance Y1 must be sufficiently far so that RF carrier signal RFC does not cause a saturation in second antenna 116.

Figure 10:
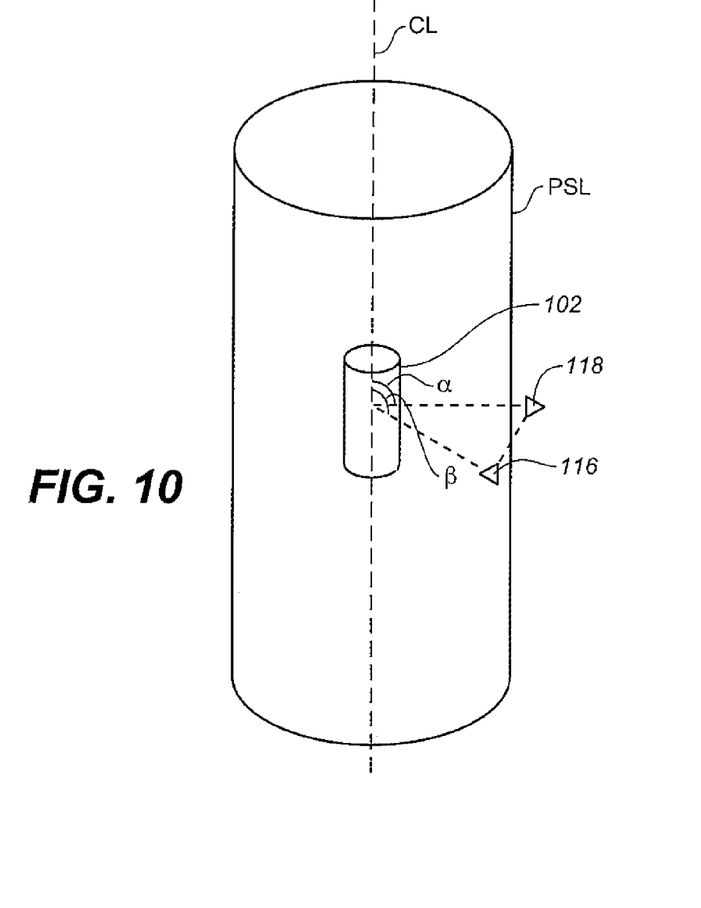
FIG. 10 is a simplified perspective schematic diagram depicting an implanted stent being interrogated by a first and second antenna disposed immediately adjacent to a portion of a user's skin layer wherein a center line of the stent is parallel to the portion of the user's skin layer.
Figure 11:
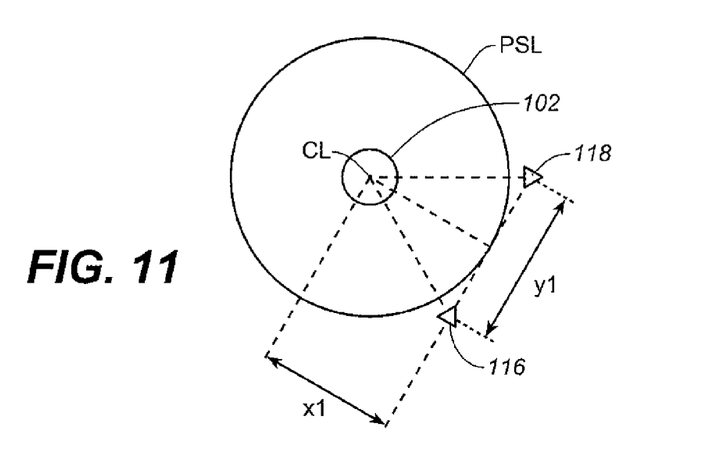
FIG. 11 simplified cross-sectional plan view corresponding to FIG. 10.
Figure 12:
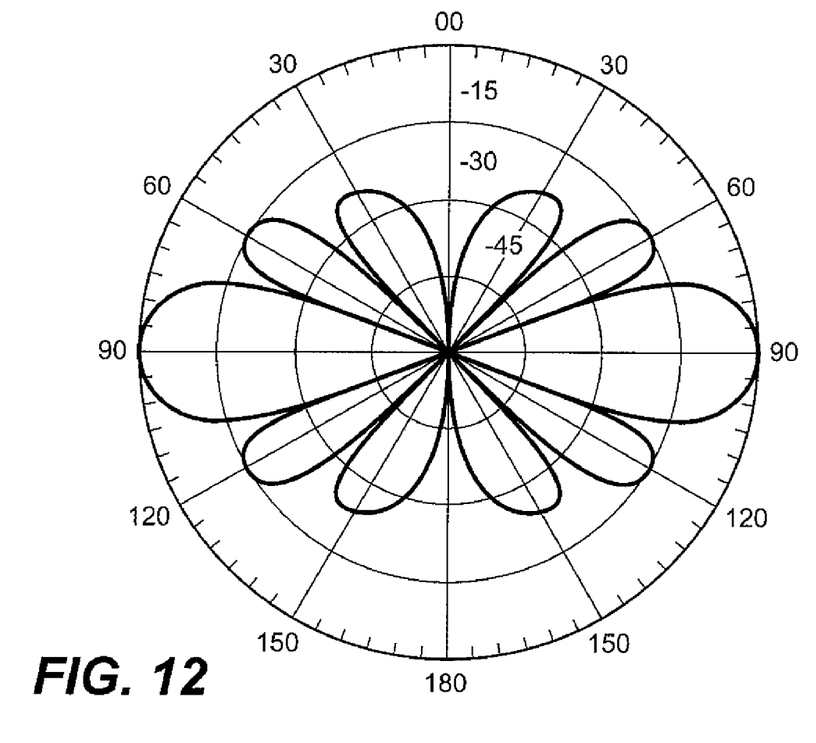
FIG. 12 is a simplified two-dimensional graph illustrating attenuation of an RF carrier signal after being reflected at a spectrum of angles for a configuration wherein a center line of a stent is orientated parallel to a portion of a user's skin layer.
Figure 13:
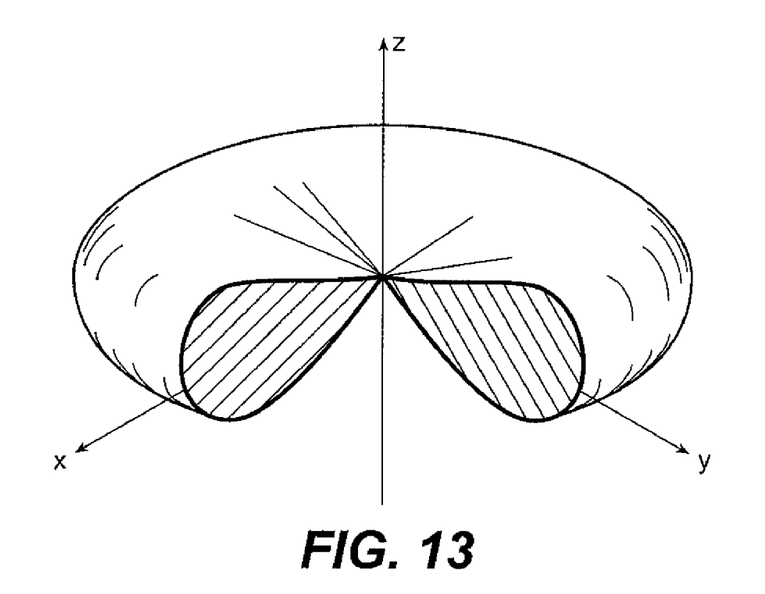
FIG. 13 is a simplified three-dimensional graph (corresponding to FIG. 12) illustrating a toroidal-shaped lobe that has the lowest attenuation of the RF carrier signal after being reflected at a spectrum of angles.

FIG. 10 is a simplified perspective schematic diagram depicting an implanted stent 102 being interrogated by a first and second antenna (116 and 118) disposed immediately adjacent to a portion of a user's skin layer PSL wherein a center line of stent 102 is parallel to the portion of the user's skin layer PSL. FIG. 11 simplified cross-sectional plan view corresponding to FIG. 10. FIG. 12 is a simplified two-dimensional graph illustrating attenuation of an RF carrier signal after being reflected at a spectrum of angles for a configuration wherein a center line of a stent is orientated parallel to a portion of a user's skin layer. FIG. 13 is a simplified three-dimensional graph (corresponding to FIG. 12) illustrating a toroidal-shaped lobe that has the lowest attenuation of the RF carrier signal after being reflected at a spectrum of angles FIG. 13 indicates that a lobe having the lowest attenuation of RF carrier signal RFC has a doughnut (toroidal) shape in three dimensions. The center line CL of stent 102 is coincident with a line formed along the 0 degree and 180 degree portion of FIG. 12. Modulated signal MS has two narrow angular ranges with a relatively low amount of attenuation (e.g., less than about −3 dB). The two narrow angular ranges are both at approximately 90 degrees (see FIGS. 12 and 13).

In the orientation of FIGS. 10-13, first antenna 116 directs RF carrier signal RFC towards stent 102 at an RF carrier signal angle β with respect to center line CL (see FIG. 10 in particular). Second antenna 118 receives modulated signal MS, which is reflected from stent 102, at a modulated signal angle α with respect to the center line CL. Based on the attenuation of modulated signal MS as depicted in FIG. 12, both first antenna 116 and second antenna 118 are preferably positioned such that RF carrier signal angle β and modulated signal angle α are approximately 90 degrees.

The distances X1 and Y1 for a stents that have a center line CL perpendicular to a portion of a user's skin layer are similar in magnitude to stents having a center line CL parallel to a portion of a user's skin layer PSL. For example, stent 102 may be implanted at a distance X1 underneath a portion of user's skin layer PSL ranging from about 5 millimeters to about 40 millimeters, and preferably between about 20 millimeters to about 30 millimeters when the center line CL of the stent is parallel to the user's skin layer. Distance Y1, which separates first antenna 116 and second antenna 118, can be, for example, in the range of from about 5 millimeters to about 50 millimeters, and preferably may be about 25 millimeters when the center line CL of the stent is parallel to the user's skin layer.

Figure 14:
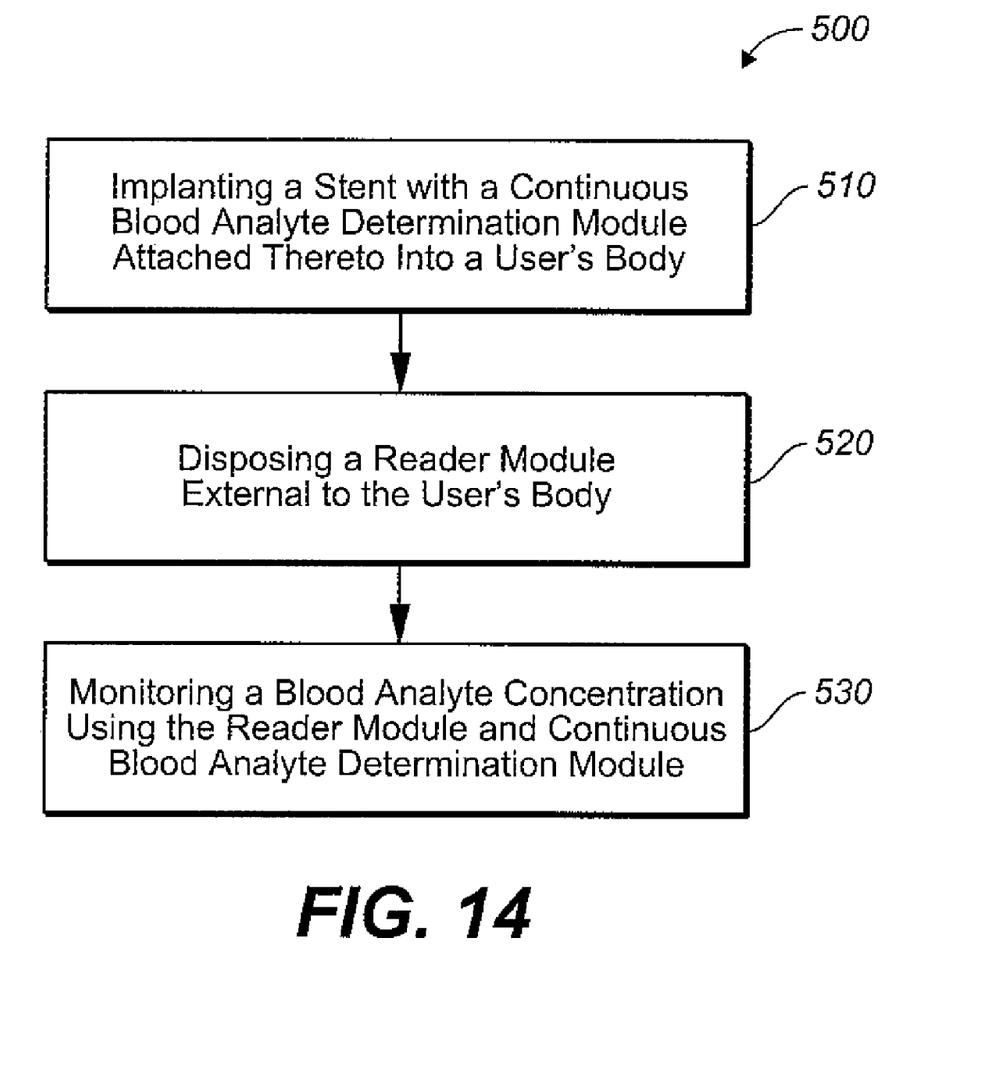
FIG. 14 is a flow diagram depicting stages in process according to an exemplary embodiment of the present invention.

FIG. 14 is a flow diagram depicting stages in method 500 for the integrated facilitization of blood flow and monitoring of blood analyte concentration according to an embodiment of the present invention. Method 500 includes implanting a stent configured for implantation into a cardiovascular system of a user's body, as set forth in step 510. Moreover, the stent implanted at step 510 has a longitudinal centerline, is configured to facilitate blood flow and has attached thereto a continuous blood analyte determination module of a blood analyte monitoring system.

Subsequently, at step 520 of method 500, a reader module of the blood analyte monitoring system is disposed external to the user's body and in proximity to a portion of the user's skin layer. At step 530, a blood analyte concentration is monitored using the reader module and continuous blood analyte determination module. The blood analyte concentration can be monitored by, for example, the following:

(i) emitting an RF carrier signal from the reader module toward the stent;

(ii) receiving the RF carrier signal at a reflection antenna of the continuous blood analyte determination module;

(iii) reflecting a modulated signal by the reflection antenna wherein the modulated signal is encoded with a blood analyte concentration determined by a sensor of the continuous blood analyte determination module;

(iv) receiving the modulated signal by the reader module; and (v) decoding the analyte concentration from the modulated signal by the reader module.

Once apprised of the present disclosure, one skilled in the art will recognize that method 500 can be practiced using systems according to embodiments of the present invention. Therefore, any of the functional characteristics and benefits described with respect to systems according to the present invention can be incorporated into method 500.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. A method for the integrated facilitization of blood flow and monitoring of blood analyte concentration comprising:
　　implanting a stent configured for implantation into a cardiovascular system of a user's body, the stent having a longitudinal centerline and configured to facilitate blood flow, the stent having attached thereto a continuous blood analyte determination module of a blood analyte monitoring system;
　　disposing a reader module of the blood analyte monitoring system external to the user's body and in proximity to a portion of the user's skin layer;
　　monitoring a blood analyte concentration using the reader module and the continuous blood analyte determination module,
　　wherein the monitoring step is accomplished by:
　　　　emitting an RF carrier signal from a first antenna of the reader module toward the stent;
　　　　receiving the RF carrier signal at a reflection antenna of the continuous blood analyte determination module;
　　　　reflecting a modulated signal by the reflection antenna wherein the modulated signal is encoded with a blood analyte concentration determined by a sensor of the continuous blood analyte determination module;
　　　　receiving the modulated signal by a second antenna of the reader module; and
　　　　decoding the analyte concentration from the modulated signal by the reader module; and
　　wherein the first antenna and second antenna are configured such that an RF carrier signal angle β and a modulated signal angle α are both less than about 30 degrees with respect to the stent center line.

2. The method of claim 1 wherein the reader module emits an RF carrier signal that is essentially perpendicular to the portion of the user's skin layer.

3. The method of claim 1 wherein the implanting step implants the stent such that the longitudinal centerline is essentially perpendicular to the portion of the user's skin layer.

4. The method of claim 1 wherein the first antenna is separated from the second antenna by a distance in the range of about 5 millimeters to about 50 millimeters.

5. The method of claim 1, wherein the disposing step is accomplished by disposing the reader module immediately adjacent to the portion of the user's skin layer.

6. A method for the integrated facilitization of blood flow and monitoring of blood analyte concentration comprising:

implanting a stent configured for implantation into a cardiovascular system of a user's body, the stent having a longitudinal centerline and configured to facilitate blood flow, the stent having attached thereto a continuous blood analyte determination module of a blood analyte monitoring system;

disposing a reader module of the blood analyte monitoring system external to the user's body and in proximity to a portion of the user's skin layer;

monitoring a blood analyte concentration using the reader module and the continuous blood analyte determination module, wherein the monitoring step is accomplished by:

emitting an RF carrier signal from the reader module toward the stent;

receiving the RF carrier signal at a reflection antenna of the continuous blood analyte determination module;

reflecting a modulated signal by the reflection antenna wherein the modulated signal is encoded with a blood analyte concentration determined by a sensor of the continuous blood analyte determination module;

receiving the modulated signal by a second antenna of the reader module; and decoding the analyte concentration from the modulated signal by the reader module; and wherein the first antenna and second antenna are configured such that an RF carrier signal angle $\beta$ and a modulated signal angle $\alpha$ are both approximately 90 degrees with respect to the stent center line.

7. The method of claim 6 wherein the implanting step implants the stent such that the longitudinal centerline is essentially parallel to the portion of the user's skin layer.

8. The method of claim 6 wherein the first antenna is separated from the second antenna by a distance in the range of about 5 millimeters to about 50 millimeters.

9. The method of claim 6, wherein the disposing step is accomplished by disposing the reader module immediately adjacent to the portion of the user's skin layer.

* * * * *